(12) United States Patent
Bresciani et al.

(10) Patent No.: US 7,051,573 B2
(45) Date of Patent: May 30, 2006

(54) GAS SENSOR CHAMBER AND ODOR DETECTION METHOD

(75) Inventors: Andrea Bresciani, Faenza (IT); Andrea Ravagnani, Imola (IT); Fabio Nardini, Fano (IT)

(73) Assignee: Sacmi Cooperativā Meccanici Imola Societa' Cooperativā, Bologna (IT)

( * ) Notice: Subject to any disclaimer, the term of this patent is extended or adjusted under 35 U.S.C. 154(b) by 0 days.

(21) Appl. No.: 10/753,561

(22) Filed: Jan. 9, 2004

(65) Prior Publication Data
US 2004/0244465 A1    Dec. 9, 2004

(30) Foreign Application Priority Data
Jun. 6, 2003    (IT)    .......................... BO2003A0348

(51) Int. Cl.
*G01N 33/497*    (2006.01)
(52) U.S. Cl. ...................... 73/23.34; 73/23.2
(58) Field of Classification Search .............. 73/23.2, 73/23.34
See application file for complete search history.

(56) References Cited

U.S. PATENT DOCUMENTS

| | | | | |
|---|---|---|---|---|
| 2,387,550 A | * | 10/1945 | Winkler | ....................... 250/283 |
| 3,882,713 A | * | 5/1975 | Nishida et al. | ............ 73/23.34 |
| 5,018,395 A | * | 5/1991 | Hickox et al. | ............ 73/864.34 |
| 5,177,994 A | * | 1/1993 | Moriizumi et al. | ........ 73/23.34 |
| 5,495,747 A | * | 3/1996 | Herman et al. | ............ 73/23.21 |
| 6,015,533 A | * | 1/2000 | Young et al. | .................. 422/83 |
| 6,085,576 A | * | 7/2000 | Sunshine et al. | .......... 73/29.01 |
| 6,516,653 B1 | | 2/2003 | Schroder | |
| 6,606,897 B1 | * | 8/2003 | Koyano et al. | ............... 73/23.2 |
| 2002/0002857 A1 | | 1/2002 | Aoyama et al. | |
| 2002/0092339 A1 | | 7/2002 | Lee et al. | |
| 2002/0124631 A1 | | 9/2002 | Sunshine et al. | |

FOREIGN PATENT DOCUMENTS

| | | |
|---|---|---|
| DE | 100 00 738 A1 | 7/2001 |
| WO | WO 01/23883 A1 | 4/2001 |

OTHER PUBLICATIONS

Patent Abstracts of Japan, vol. 1999, No. 1, Jan. 29, 1999; JP 10 267879 A (Shimadzu Corp.); Abstract; Figures 1-6.

* cited by examiner

Primary Examiner—Michael Cygan
(74) Attorney, Agent, or Firm—Squire, Sanders, Dempsey LLP

(57) ABSTRACT

The invention relates to a chamber (2) for gas sensors (9) to be used in a device (1) for detecting aromas or odors. The chamber (2) comprises three portions (5, 6, 7) in which there is a uniform, turbulence-free flow (F) of gas or vapors to be analyzed, and at least one gas sensor (9) positioned in the central portion in such a way as to be immersed in and to laterally and tangentially interact with the flow (F). The chamber (2) also comprises a heating and temperature regulating device (16, 17). The invention also relates to an odor detection method which comprises a step in which a uniform, turbulence-free flow (F) of gas or vapor interacts with a gas sensor (9) laterally and tangentially.

41 Claims, 3 Drawing Sheets

GAS SENSOR CHAMBER AND ODOR DETECTION METHOD

BACKGROUND OF THE INVENTION

The present invention relates to a gas sensor chamber and an odor detection method that uses the chamber according to the invention.

One non-limiting example of an application of the chamber according to the invention is in apparatus for detecting aromas or odors produced by food products. This specification expressly refers to uses of this kind but without thereby restricting the scope of the invention.

Apparatus for detecting the aromas or odors produced by food products is used to check the quality of a food product not only in terms of the constancy of its properties during the preparation process but also to detect aging or spoiling.

This type of check is very useful because it provides information quickly without having to come into contact with the product to be checked.

Devices are known which detect aromas or odors using artificial sensors that work in a manner similar to the olfactory system of mammals.

Chemical resistors are one example of sensors of this kind. This type of sensor is made from special materials that absorb the gas/vapor to be detected and produce a change in electrical resistance.

The substance absorbed by the sensor material produces a change in the resistance to the passage of current through an electrical circuit to which the sensor is connected.

Usually, the sensors used for olfactory measurement analysis are transducers which convert an interaction with defined gaseous substances into electrical signals.

Each sensor is differently sensitive to a specific group of gaseous substances and therefore, to produce an "odor print", that is to say, a specific aroma or odor, with satisfactory precision, several olfactory sensors are required, each differently sensitive to that specific group of gaseous substances.

Further, once the sensors used to identify gas mixtures have generated a certain signal, they must be cleared of the gas they have absorbed before they can proceed to carrying out another analysis.

It follows that the arrangement of the sensors and the shape of the chamber in which the sensors are located are very important factors for the correct identification of the odor or aroma.

One gas sensor arrangement is known from patent U.S. Pat. No. 6,516,653-B2.

That document describes an apparatus device comprising one or more gas or vapor sensors located in a room where concentrations or mixtures of gases or vapors have to be monitored, and with a diffusion body placed in front of the sensors.

According to the invention described in that document, the gas sensors, whose responsiveness is influenced by the design of the container enclosing the space to be monitored, by contamination or by static conditions in the space to be monitored, are positioned in a duct where a flow that accelerates the diffusion of the gases or vapors to be analyzed is generated, thus increasing the responsiveness of the gas sensors.

SUMMARY OF THE INVENTION

One aim of the present invention is to provide an improved gas sensor chamber permitting optimum operation of the gas sensors.

Another aim of the present invention is to provide a gas sensor chamber housing one or more sensors in such a way that all the sensors are in the same detection conditions.

A further aim of the present invention is to provide a gas sensor chamber permitting rapid detection of the signals produced by the gaseous substances and fast resetting of the sensors so they are ready to carry out the next analysis.

According to one aspect of it, the present invention provides a gas sensor chamber as defined in claim 1.

Yet another aim of the present invention is to provide an improved method for detecting odors in which a uniform flow of the gases or vapors to be analyzed is made to interact laterally and tangentially with the gas sensors.

According to another aspect of it, the present invention provides a gas detection method as defined in claim 18.

The dependent claims describe preferred, advantageous embodiments of the invention.

BRIEF DESCRIPTION OF THE DRAWINGS

The preferred embodiments of the invention will now be described, without restricting the scope of the inventive concept, with reference to the accompanying drawings in which.

DESCRIPTION OF THE PREFERRED EMBODIMENTS

Figure 1:
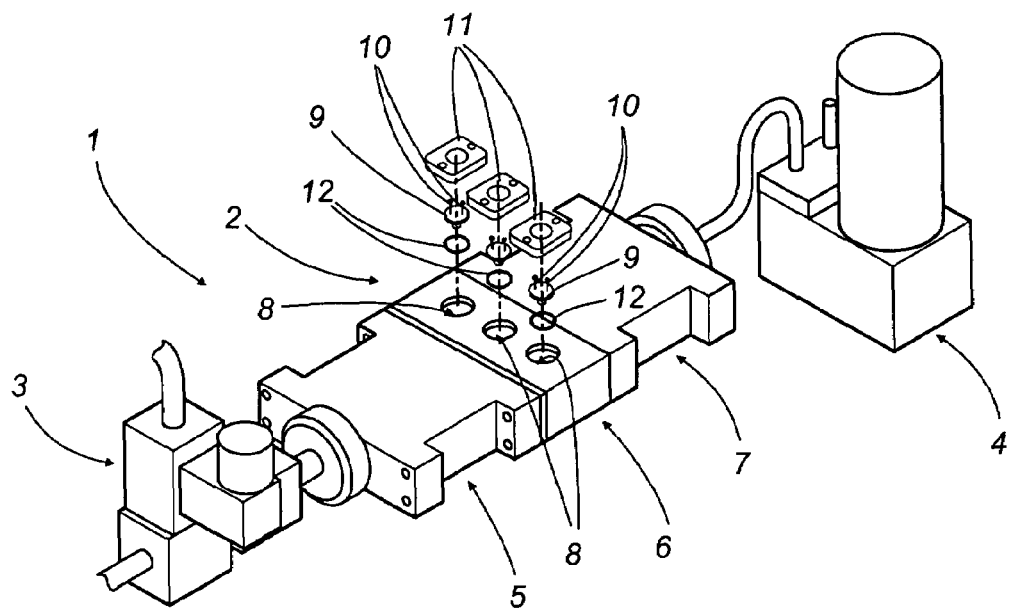
FIG. 1 is an axonometric view of an odor detection device equipped with a gas sensor chamber made according to the present invention.

With reference to the accompanying drawings, the odor detection device equipped with the gas sensor chamber according to the invention is denoted in its entirety by the numeral 1.

The device 1 essentially comprises a gas sensor chamber 2 and a diverter valve 3 with two connections—a first connection to a zone in which the product to be checked is located and a second connection to a neutral reference gas—and a pump 4 to suck the reference gas or the air from the zone where the product to be checked is located.

The diverter valve 3 and the suction pump 4 do not form part of the subject-matter of the present invention and, for this reason, are illustrated schematically in FIG. 1.

As shown in the drawings, the chamber 2 comprises an inlet 2a and an outlet 2b for the flow F of gas or vapor to be analyzed, a divergent portion 5, a central sensor mounting portion 6 and a convergent portion 7.

Figure 2:
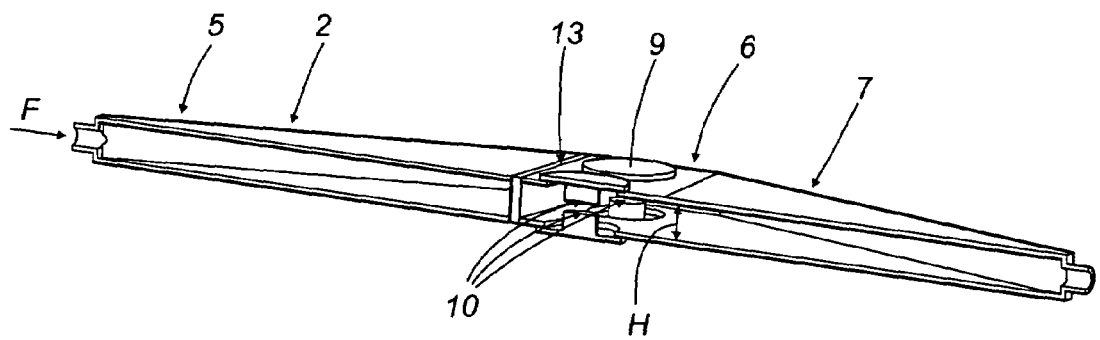
FIG. 2 is a schematic section view of the gas sensor chamber made according to the present invention.
Figure 3:
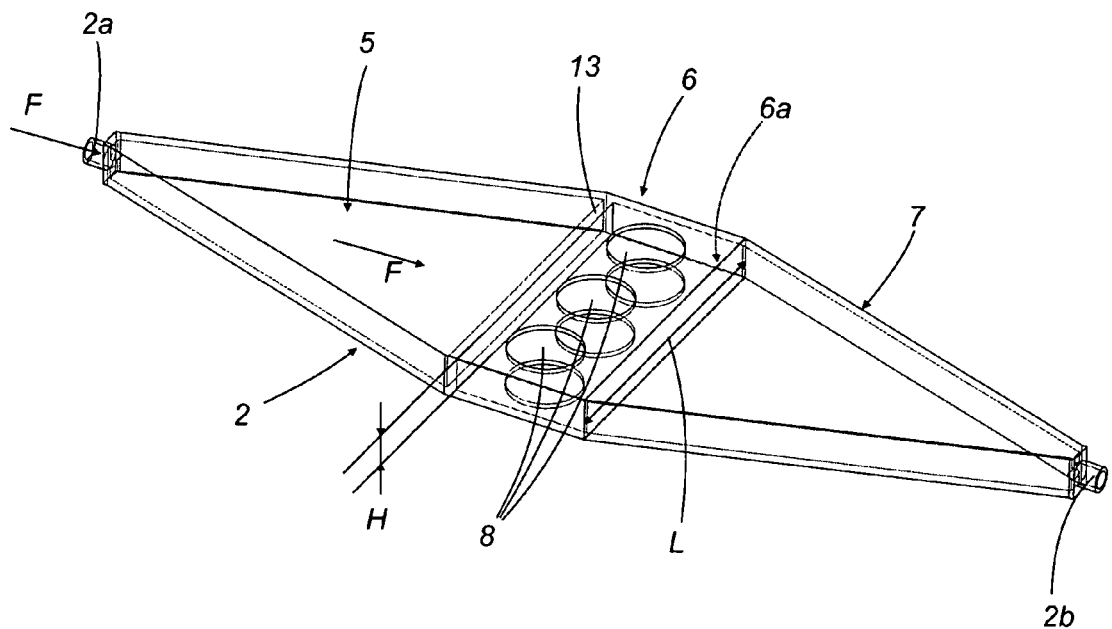
FIG. 3 is a schematic axonometric view of the gas sensor chamber illustrated in the figures listed above.

The central portion 6 has a total internal height H and presents a lateral surface 6a, of width L, on which there is at least one hole 8 with a respective gas sensor 9 fitted in it. The sensor 9 has a sensitive surface 10 located inside the central portion 6 in such a way as to interact tangentially with the flow F of gas or vapors to be analyzed. More specifically, as illustrated in FIG. 2, the sensitive surface 10 is located approximately a third of the way up or down the total height H of the central portion 6.

The central portion 6 has an elongate, rectangular shaped cross section so as to maximize the ratio of the area of the lateral surface 6a to the internal volume.

According to a preferred embodiment of the invention, the central portion 6 houses six gas sensors 9 arranged in groups of three along the top and bottom of the long sides of the lateral surface 6a in a direction transversal to the flow F of gas or vapors to be analyzed.

As mentioned above, the sensitive surfaces 10 of the sensors 9 at the top are located about a third of the way down the total height H of the central portion 6, whilst the surfaces 10 of the sensors 9 at the bottom are located about a third of the way up the total height H of the central portion 6.

In this way, the sensitive surfaces 10 of the sensors 9 all interact with the flow F in the same way and without interfering with each other. Since each sensor 9 is differently sensitive to a specific odorous mixture, this arrangement makes it possible to identify the odor print in a precise and repeatable manner.

The elongate flattened shape of the central portion 6, with a height H that is relatively small compared to its width L, is advantageous for rapid detection of the odor or aroma because it minimizes the volume or gas or vapor to be analyzed relative to the size of the sensitive surfaces 10 of the sensors 9, thus allowing a high concentration of odor or aroma inside the chamber 2.

The ratio of the width L to the height H (L/H) of the central portion 6 may be between 8 and 12 and is preferably 9.

The sensitive surface 10 of each sensors 9—since it is inside the central portion 6 approximately a third of the way along the height H—interacts in optimum manner with the flow F of the gas or vapor and is not disturbed by the lateral surface 6a of the central portion 6.

In the preferred embodiment, there are six sensors. This is a purely exemplary number and is a compromise between the need to precisely identify the odor print and the cost and size of the odor detection device in its entirety.

It will therefore be understood that sensor chambers 2 according to the invention can be made with a larger or smaller number of sensors without departing from the scope of the inventive concept as defined in the claims.

Figure 5:
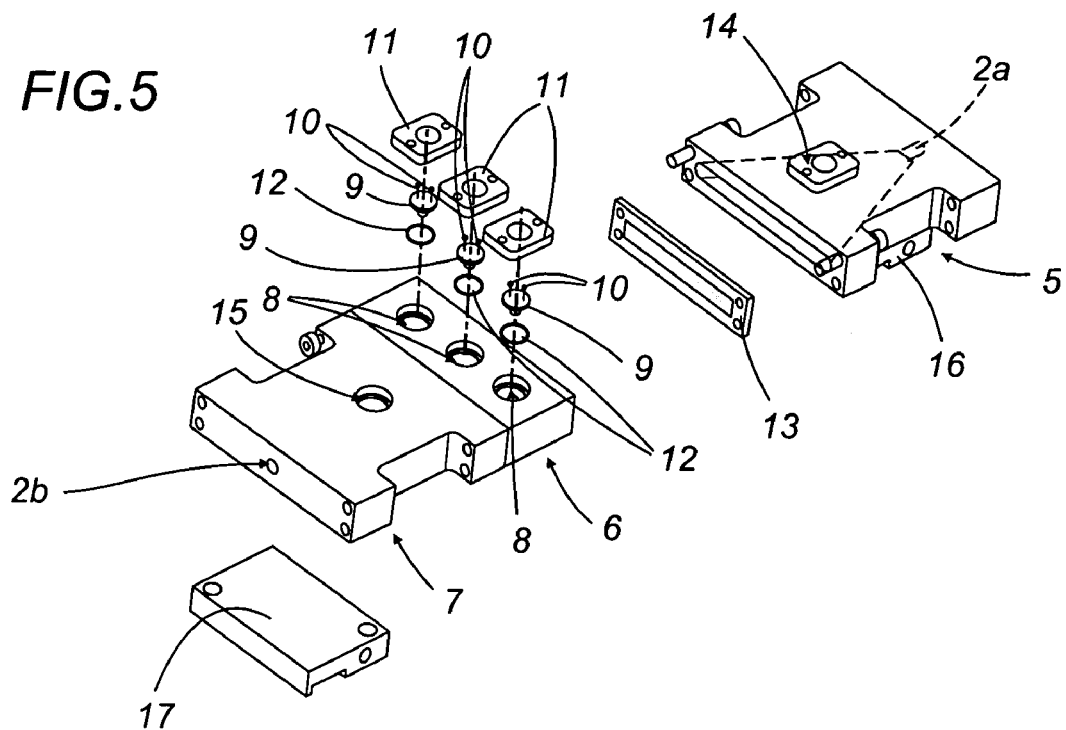
FIG. 5 is an axonometric view of a constructional form of the gas sensor chamber according to the present invention.
Figure 6:
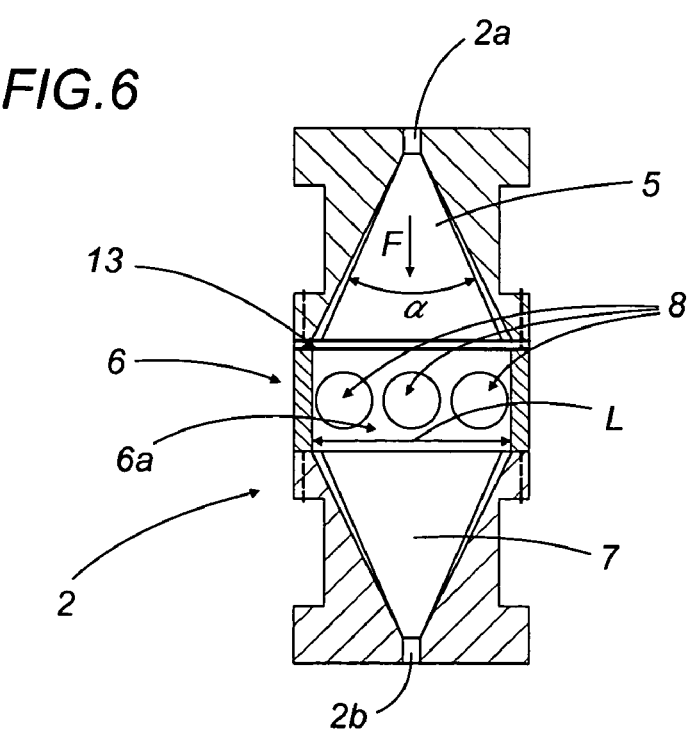
FIG. 6 is a longitudinal section view of the gas sensor chamber illustrated in FIG. 5.

As illustrated in FIG. 5, each sensor 9 is fixed to the central portion 6 by a plate 11 and screws, and also has a seal 12, such as an O-ring, to prevent infiltration of air from the outside environment. The holes 8 in which the sensors 9 are fitted are shape or size coded so that each sensor has a fixed position in the chamber 2 and cannot be changed round with any of the others. For example, the holes 8 may have a different diameter and/or geometrical shape, matching the diameter and/or shape of the couplings on the respective sensors 9.

The divergent portion 5 connects the inlet 2a, which is normally circular, with the central portion 6, which has an elongate cross section.

The divergent portion 5 must also create a flow of gas or vapor that is as uniform and free of turbulence as possible.

To achieve this, the divergent portion 5 has a flattened conical shape with an angle α of less than 12 degrees at the vertex of the cone. Larger angles α—around 50 degrees—are also possible but, in this case, a diffuser or uniformizer 13 must be fitted to correctly address or redirect the gas flow.

As a result, the cone angle α of the divergent portion 5 may fall within either of two possible ranges: angle α from 0 to 12 degrees without diffuser or uniformizer 13, or angle α from 40 to 65 degrees with diffuser or uniformizer 13.

In a preferred embodiment with diffuser or uniformizer, the cone angle α is 52 degrees.

The flow diffuser or uniformizer 13 may be made from fine metallic mesh which straightens and uniformizes the passage of the flow F into the central portion 6.

The flow diffuser 13 presents an open area between 30 and 40% with a mesh size of between 300 and 500 μm (microns). In a preferred embodiment, the open area is 35% and the mesh size 380 μm (microns).

Alternatively, porous polymer membranes may be used, even ones capable of filtering out specific gaseous substances.

The novel feature of this chamber is the way in which the gas or vapor flow F interacts with the sensors 9, namely, laterally and tangentially, enabling the sensors 9 to work better.

That is because the interaction between the sensors 9 and the gases analyzed occurs through a reaction on the surface of the sensors 9 and, consequently, tangential flow maximizes the responsiveness of the sensors 9.

Figure 4:
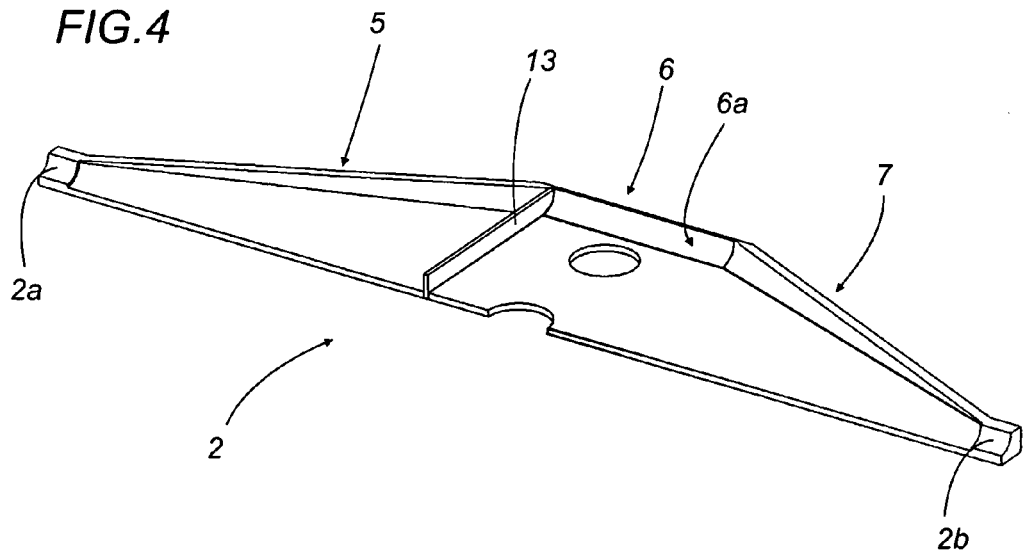
FIG. 4 is a schematic section view of another embodiment of the gas sensor chamber according to the present invention.

FIG. 4 illustrates an embodiment of the chamber 2 where the lateral surface 6a has smooth, rounded corners and edges all the way around it.

The convergent portion 7 may be made with the same geometrical characteristics as the divergent portion 5, which means that the two portions 5 and 7 may be identical, with obvious advantages in terms of production cost.

The portions 5, 7 may also have housings 14, 15 for other sensors, such as, for example, sensors to detect temperature and relative humidity in the chamber 2.

In fact, it should be remembered that for optimum operation, the sensors 9 may need to be heated and that, since the temperature and relative humidity in the chamber 2 affect the precision of odor detection, it is necessary to know and, if possible, control and modify these conditions in the chamber 2. To maintain uniform detection conditions, the chamber 2 may have heat insulation and the divergent and convergent portions 5, 7 may be equipped with heaters 16, 17 attached to said portions 5, 7.

The heaters 16, 17 thus constitute a device for heating and regulating the temperature of the chamber 2 and may be based on embedded resistors or cartridges.

The materials from which the chamber 2 is made must have good properties of inertia and resistance to absorption of aromas and odors so as not to affect detection by the sensors 9. They must also have a good resistance to relatively high temperatures.

That is because certain types of sensors 9 must be heated to temperatures of around 300–500 degrees Celsius to work efficiently. The chamber 2 may thus need to be heated by the heaters 16, 17 to temperatures around 50–80 degrees Celsius.

For these reasons, the chamber 2 may be made, for example, from stainless steel, type AISI 304, and the seals between the different parts of the chamber 2 may be made from polytetrafluoroethylene, usually known as Teflon, a registered trademark of the Du Pont company.

The invention also concerns an odor detection method comprising the following steps:

sucking in the gas or vapor to be analyzed from the area where the product is located;

generating a uniform turbulence-free flow F of gas or vapor into a sensor mounting portion 6;

making the flow F of gas or vapor interact laterally and tangentially with sensors 9;

collecting the signals generated by the sensors 9 and processing them to define the odor print of the gas or vapor to be analyzed;

sucking in a neutral reference gas;

generating a uniform turbulence-free flow F of the neutral reference gas into the sensor mounting portion 6;

making the flow F of reference gas interact laterally and tangentially with the sensors 9 so as to clear the previously analyzed gas or vapor from the sensors 9 and make the sensors 9 ready to carry out another analysis.

The odor detection method also comprises steps of measuring temperature and of controlling the temperature by heating the sensors 9 and the chamber 2.

The invention has important advantages.

The chamber according to the invention is made in such a way that all the sensors 9 interact simultaneously with the same flow of gas or vapor to be analyzed, the flow, in all cases, varying very little from sensor to sensor.

The chamber according to the invention is shaped to permit quick and easy clearing after each analysis carried out.

The volume of the gas or vapor sample to be analyzed is reduced in relation to the geometrical and constructional constraints due to the sensors, pipe fittings and electrical connectors.

Chamber design is such that each sensor has a single, well-defined and easily identifiable mounting position.

The heat insulation, made to the measure of the chamber 2, and the embedded resistor or cartridge heating system create constantly optimum conditions for detection.

The compact shape of the chamber 2 can be reduced in size without altering its geometry and leaving unchanged the advantages described above.

The invention as described above may be modified and adapted in several ways without thereby departing from the scope of the inventive concept as defined in the claims.

Moreover, all the details of the invention may be substituted by technically equivalent elements.

What is claimed is:

1. A chamber for gas sensors in a device for detecting aromas or odors, the device including a container in which there is a flow of gas or vapors to be analyzed, the chamber comprising: an inlet through which the flow flows in; an outlet through which the flow flows out; a plurality of gas sensors each having a sensitive surface positioned in such a way as to be immersed in and to laterally interact with the flow; whereby each sensor detects a signal usable to identify the kind of gas or vapor to be analyzed; wherein the chamber further comprises a central portion having a total internal height and a lateral surface, of width L, on which there is at least one hole with a respective gas sensor fitted in it; said gas sensors being arranged along a top and a bottom of long sides of the lateral surface of the central portion.

2. The chamber for gas sensors according to claim 1, wherein the sensitive surface of each gas sensor is positioned in such a way as to laterally and tangentially interact with the flow.

3. The chamber for gas sensors according to claim 1, wherein the central portion has a width to height ratio between 8 and 12.

4. The chamber for gas sensors according to claim 1, wherein the central portion has a width to height ratio equal to 9.

5. The chamber for gas sensors according to claim 1, wherein the sensitive surface of the sensor is positioned approximately a third of the way along the height of the central portion.

6. The chamber for gas sensors according to claim 1, further comprising a divergent portion having a flattened conical shape with an angle at the vertex of the cone, the portion connecting the inlet to the central portion.

7. The chamber for gas sensors according to claim 6, wherein the divergent portion has a cone angle between 0 and 12 degrees.

8. The chamber for gas sensors according to claim 1, further comprising: a divergent portion having a flattened conical shape with an angle between 40 and 65 degrees at the vertex of the cone, the portion connecting the inlet to the central portion; and a diffuser or uniformizer located between the divergent portion and the central portion.

9. The chamber for gas sensors according to claim 8, wherein the divergent portion has a cone angle equal to 52 degrees.

10. The chamber for gas sensors according to claim 8, further comprising a convergent portion having a flattened conical shape, the convergent portion connecting the central portion to the outlet.

11. The chamber for gas sensors according to claim 10, wherein the convergent portion is substantially equal to the divergent portion.

12. The chamber for gas sensors according to claim 8, further comprising a heating and temperature regulating device.

13. The chamber for gas sensors according to claim 8, wherein the diffuser or uniformizer is made from fine metallic mesh which straightens and uniformizes the passage of the flow into the central portion.

14. The chamber for gas sensors according to claim 8, wherein the flow diffuser or uniformizer has an open area between 30 and 40% and a mesh size between 300 and 500 µm.

15. The chamber for gas sensors according to claim 8, wherein the flow diffuser or uniformizer has an open area of 35% and a mesh size of 380 µm.

16. The chamber for gas sensors according to claim 8, wherein the flow diffuser or uniformizer is made from porous polymer membranes.

17. The chamber for gas sensors according to claim 8, wherein the flow diffuser or uniformizer is made from porous polymer membranes having selective filtering properties in relation to specific gaseous substances.

18. A chamber for gas sensors in a device for detecting aromas or odors, the device including a container in which there is a flow of gas or vapors to be analyzed, the chamber comprising: an inlet through which the flow flows in; an outlet through which the flow flows out; a central portion having a total internal height and a lateral surface, of width L, on which there is at least one hole; a divergent portion having a flattened conical shape with an angle at the vertex of the cone, the portion connecting the inlet to the central portion; a plurality of gas sensors each having a sensitive surface positioned in the at least one hole in such a way as to be immersed in and to laterally interact with the flow; whereby each sensor detects a signal usable to identify the kind of gas or vapor to be analyzed; said gas sensors being arranged along a top and a bottom of long sides of the lateral surface of the central portion.

19. The chamber for gas sensors according to claim 18, wherein the divergent portion has a cone angle between 0 and 12 degrees.

20. The chamber for gas sensors according to claim 18, wherein the divergent portion has a cone angle between 40 and 65 degrees and the chamber further comprises a diffuser or uniformizer located between the divergent portion and the central portion.

21. The chamber for gas sensors according to claim 20, wherein the divergent portion has a cone angle equal to 52 degrees.

22. The chamber for gas sensors according to claim 18, further comprising a diffuser or uniformizer located between the divergent portion and the central portion.

23. The chamber for gas sensors according to claim 22, wherein the diffuser or uniformizer is made from fine metallic mesh which straightens and uniformizes the passage of the flow into the central portion.

24. The chamber for gas sensors according to claim 22, wherein the flow diffuser or uniformizer has an open area between 30 and 40% and a mesh size between 300 and 500 μm.

25. The chamber for gas sensors according to claim 22, wherein the flow diffuser or uniformizer has an open area of 35% and a mesh size of 380 μm.

26. The chamber for gas sensors according to claim 22, wherein the flow diffuser or uniformizer is made from porous polymer membranes.

27. The chamber for gas sensors according to claim 22, wherein the flow diffuser or uniformizer is made from porous polymer membranes having selective filtering properties in relation to specific gaseous substances.

28. The chamber for gas sensors according to claim 18, further comprising a convergent portion having a flattened conical shape, the convergent portion connecting the central portion to the outlet.

29. The chamber for gas sensors according to claim 18, wherein the convergent portion is substantially equal to the divergent portion.

30. The chamber for gas sensors according to claim 18, further comprising a heating and temperature regulating device.

31. A chamber for gas sensors in a device for detecting aromas or odors, the device including a container in which there is a flow of gas or vapors to be analyzed, the chamber comprising: an inlet through which the flow flows in; an outlet through which the flow flows out; a central portion having a total internal height and a lateral surface, of width L, on which there is at least one hole; a divergent portion having a flattened conical shape with a angle at the vertex of the cone, the portion connecting the inlet to the central portion; a convergent portion having a flattened conical shape, the convergent portion connecting the central portion to the outlet; a plurality of gas sensors each having a sensitive surface positioned in the at least one hole in such a way as to be immersed in and to laterally interact with the flow; whereby each sensor detects a signal usable to identify the kind of gas or vapor to be analyzed; said gas sensors being arranged along a top and a bottom of long sides of the lateral surface of the central portion.

32. The chamber for gas sensors according to claim 31, wherein the divergent portion has a cone angle between 0 and 12 degrees.

33. The chamber for gas sensors according to claim 31, wherein the divergent portion has a cone angle between 40 and 65 degrees and the chamber further comprises a diffuser or uniformizer located between the divergent portion and the central portion.

34. The chamber for gas sensors according to claim 33, wherein the divergent portion has a cone angle equal to 52 degrees.

35. The chamber for gas sensors according to claim 31, wherein the convergent portion has a cone angle between 0 and 12 degrees.

36. The chamber for gas sensors according to claim 31, wherein the convergent portion has a cone angle between 40 and 65 degrees.

37. The chamber for gas sensors according to claim 31, wherein the convergent portion has a cone angle equal to 52 degrees.

38. The chamber for gas sensors according to claim 31, wherein the convergent portion is substantially equal to the divergent portion.

39. The chamber for gas sensors according to claim 31, further comprising a heating and temperature regulating device.

40. A chamber for gas sensors in a device for detecting aromas or odors, the device including a container in which there is a flow of gas or vapors to be analyzed, the chamber comprising: an inlet through which the flow flows in; an outlet through which the flow flows out; at least one gas sensor having a sensitive surface positioned in such a way as to be immersed in and to laterally interact with the flow; at least one sensor detecting a signal usable to identify the kind of gas or vapor to be analyzed; wherein the chamber further comprises a divergent portion having a flattened conical shape with an angle between 40 and 65 degrees at the vertex of the cone, the portion connecting the inlet to the central portion; a diffuser or uniformizer, which is made from fine metallic mesh for straightening and uniforming the passage of the flow into the central portion, being located between the divergent portion and the central portion.

41. A chamber for gas sensors in a device for detecting aromas or odors, the device including a container in which there is a flow of gas or vapors to be analyzed, the chamber comprising: an inlet through which the flow flows in; an outlet through which the flow flows out; at least one gas sensor having a sensitive surface positioned in such a way as to be immersed in and to laterally interact with the flow; at least one sensor detecting a signal usable to identify the kind of gas or vapor to be analyzed; wherein the chamber further comprises a divergent portion having a flattened conical shape with an angle between 40 and 65 degrees at the vertex of the cone, the portion connecting the inlet to the central portion; a diffuser or uniformizer, which is made from porous polymer membranes, being located between the divergent portion and the central portion.

* * * * *